(12) United States Patent
Ohkuma et al.

(10) Patent No.: US 6,720,439 B1
(45) Date of Patent: Apr. 13, 2004

(54) SYNTHESIS OF RUTHENIUM-HYDRIDE COMPLEXES AND PREPARATION PROCEDURES OF CHIRAL ALCOHOLS AND KETONES

(75) Inventors: Takeshi Ohkuma, Aichi-gun (JP); Masatoshi Koizumi, Okaya (JP); Kilian Muñiz, Hildesheim (DE); Ryoji Noyori, Nisshin (JP)

(73) Assignee: Nagoya Industrial Science Research Institute, Nagoya (JP)

( * ) Notice: Subject to any disclaimer, the term of this patent is extended or adjusted under 35 U.S.C. 154(b) by 0 days.

(21) Appl. No.: 10/291,611

(22) Filed: Nov. 12, 2002

(51) Int. Cl.$^7$ .................. C07F 15/00; B01J 31/00; B01D 3/34; C07C 29/14
(52) U.S. Cl. .................. 556/8; 502/162; 502/167; 203/32; 568/881; 568/885; 556/21
(58) Field of Search .................. 556/8, 21; 568/881, 568/885; 502/162, 167; 203/32

(56) References Cited

U.S. PATENT DOCUMENTS 6,596,887 B2 * 7/2003 Mikami et al. ............... 556/21

FOREIGN PATENT DOCUMENTS

JP     11-189600     7/1999

\* cited by examiner

Primary Examiner—Porfirio Nazario-Gonzalez
(74) Attorney, Agent, or Firm—Oblon, Spivak, McClelland, Maier & Neustadt, P.C.

(57) ABSTRACT trans-RuH($\eta^1$-BH$_4$)[(S)-xylbinap][(S,S)-dpen] (0.00125 mmol), acetophenone (5.0 mmol), and 2-propanol (2.5 mL) were placed in an autoclave, and the resulting solution was repeatedly subject 5 times to a procedure of performing pressure reduction and argon introduction while stirring the solution for deaeration. A hydrogen tank was then connected to the autoclave, and after replacing the air inside an introduction tube with hydrogen, the pressure inside the autoclave was adjusted to 5 atmospheres and then hydrogen was released until the pressure dropped to 1 atmosphere. After repeating this procedure 10 times, the hydrogen pressure was adjusted to 8 atmospheres and stirring at 25° C. was performed for 12 hours. By concentrating the solution obtained by depressurization and subjecting the crude product to simple distillation, (R)-1-phenylethanol (yield: 95%) in the form of a colorless oily substance was obtained at an ee of 99%.

19 Claims, No Drawings

SYNTHESIS OF RUTHENIUM-HYDRIDE COMPLEXES AND PREPARATION PROCEDURES OF CHIRAL ALCOHOLS AND KETONES

BACKGROUND OF THE INVENTION

1. Field of the Invention

This invention concerns new ruthenium hydride complexes, procedures of preparing alcohol compounds using these new complexes, and methods of separating racemic carbonyl compounds using these new complexes.

2. Description of the Prior Art

Since priorly, various methods have been known for preparing alcohol compounds by reduction of carbonyl compounds using ruthenium complexes as homogeneous catalysts. For example, in Japanese Unexamined Patent Publication No. Hei 11-189600, a ruthenium dichloride complex, having 2,2'-bis-(diphenylphosphino)-1,1'-binaphthyl, which has a C2 axis of symmetry and high chemical stability, as a phosphine ligand, is used as a chiral catalyst to reduce acetophenone under the presence of a strong base to obtain a corresponding alcohol at high enantiomeric excess and high yield.

However, since the reduction reaction using the above-mentioned ruthenium dichloride complex as a chiral catalyst is carried out under the presence of a strong base, when a base-sensitive carbonyl compound having an ester group or β-amino group, etc., is reduced, side reactions occur and an alcohol compound cannot be obtained efficiently.

SUMMARY OF THE INVENTION

An object of this invention is to provide ruthenium hydride complexes that enable efficient reduction of base-sensitive carbonyl compounds. Another object of this invention is to provide procedures of preparing alcohol compounds and methods of separating racemic carbonyl compounds using these ruthenium hydride complexes.

As a result of diligent research, the present inventors have found compounds of general formula (1) to be ruthenium hydride complexes that function as catalysts that enable reduction of carbonyl compounds without the presence of a strong base. In the present specification, a compound of general formula (1) is not restricted to a single diastereomer and may be a cis form or a trans form.

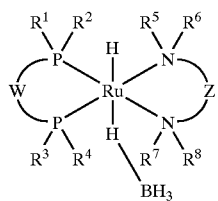

(1)

(wherein for $R^1R^2P$—W—$PR^3R^4$, W is a binaphthyl group, which is bonded to phosphorus atoms at positions 2 and 2' and may have one or more substituents at any of the other positions, each of $R^1$ to $R^4$ is the same or different hydrocarbon group that may or may not have one or more substituents, $R^1$ and $R^2$ may together form a carbon chain ring that may have one or more substituents, $R^3$ and $R^4$ may together form a carbon chain ring that may have one or more substituents, each of $R^5$ to $R^8$ is the same or different hydrocarbon group that may or may not have one or more substituents, Z is a hydrocarbon group that may or may not have one or more substituents, and each of the ligands of Ru may be positioned in any manner).

Unlike prior-art ruthenium dihalide complexes, ruthenium hydride complexes of general formula (1) enable carbonyl compounds to be reduced without the presence of a strong base and thus enable alcohol compounds to be prepared by efficient reduction of base-sensitive carbonyl compounds.

Each of the hydrocarbon groups at $R^1$ to $R^4$ of general formula (1) may have a substituent and may be an aliphatic or alicyclic hydrocarbon group that is saturated or unsaturated, amonocyclic or polycyclic aromatic or fatty aromatic hydrocarbon group, or any of various such hydrocarbon groups having substituents. Such a hydrocarbon group may be selected from the group consisting of such hydrocarbon groups as alkyl, alkenyl, cycloalkyl, cycloalkenyl, phenyl, tolyl, xylyl, naphthyl, phenylalkyl, etc., and hydrocarbon groups with any of various allowable substituents, such as alkyl, alkenyl, cycloalkyl, aryl, alkoxy, ester, acyloxy, halogen atom, nitro, and cyano groups, etc. Also, when a ring is formed by $R^1$ and $R^2$ or by $R^3$ and $R^4$, $R^1$ and $R^2$ or $R^3$ and $R^4$ may be bonded to form a carbon chain and may be selected to have any of various allowable substituents, such as alkyl, alkenyl, cycloalkyl, aryl, alkoxy, ester, acyloxy, halogen atom, nitro, and cyano groups, etc., on the carbon chain.

Examples of the amine ligand (see, general formula (2)) in general formula (1) include ethylenediamine, 1,2-diaminopropane, 1,3-diaminopropane, 1,4-diaminobutane, 2,3-diaminobutane, 1,2-cyclopentanediamine, 1,2-cyclohexanediamine, N-methylethylenediamine, N,N'-dimethylethylenediamine, N,N,N'-trimethylethylenediamine, N,N,N',N'-tetramethylethylenediamine, o-phenylenediamine, p-phenylenediamine,etc. An optically active diamine compound may also be used. Examples include such optically active diamine compounds as optically active 1,2-diphenylethylenediamine, 1,2-cyclohexanediamine, 1,2-cycloheptanediamine, 2,3-dimethylbutanediamine, 1-methyl-2,2-diphenylethylenediamine, 1-isobutyl-2,2-diphenylethylenediamine, 1-isopropyl-2,2-diphenylethylenediamine, 1-methyl-2,2-di(p-methoxyphenyl)ethylenediamine, 1-isobutyl-2,2-di(p-methoxyphenyl)ethylenediamine, 1-isopropyl-2,2-di(p-methoxyphenyl)ethylenediamine, 1-benzyl-2,2-di(p-methoxyphenyl)ethylenediamine, 1-methyl-2,2-dinaphtylethylenediamine, 1-isobutyl-2,2-dinaphthlethylenediamine, 1-isopropyl-2,2-dinaphtylethylenediamine, etc. Furthermore, the optically active diamine compounds that may be used are not limited to optically active ethylenediamine derivatives, and optically active propanediamine derivatives, butanediamine derivatives, etc., may also be used.

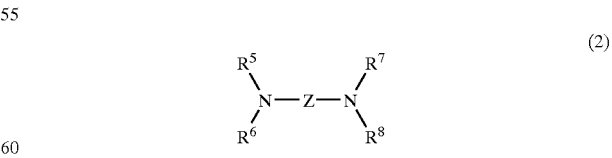

(2)

As a ruthenium complex that is to be the starting material for complex synthesis, a complex of valence, 0, 1, 2, 3 or higher valence may be used. When a zero-valent or univalent ruthenium complex is used, oxidation of ruthenium must be carried out by the final stage. When a divalent complex is used, the ruthenium complex and phosphine ligand and then the amine ligand may be reacted successively or in reverse order or simultaneously for synthesis. When a ruthenium complex with a valence of 3, 4, or greater is used as the starting material, reduction of ruthenium atom must be carried out by the final stage. A ruthenium complex indicated for example in Japanese Unexamined Patent Publication No. Hei 11-189600 may be used as the ruthenium complex that is to be the starting material, and specific examples include inorganic ruthenium compounds, such as ruthenium (III) chloride hydrate, ruthenium (III) bromide hydrate, ruthenium (III) iodide hydrate, etc., diene-liganded ruthenium compounds, such as [ruthenium dichloride (norbornadiene)] polynuclear complex, [ruthenium dichloride(cyclooctadiene)] polynuclear complex, etc., aromatic-compound-liganded ruthenium compounds, such as [ruthenium dichloride(benzene)] dinuclear complex, [ruthenium dichloride(p-cimene)] dinuclear complex, [ruthenium dichloride(trimethylbenzene)] dinuclear complex, [ruthenium dichloride(hexamethylbenzene)] dinuclear complex, etc., and phosphine-liganded complexes, such as dichlorotris(triphenylphosphine)ruthenium, etc.

The reaction of the ruthenium complex that is the starting material and a phosphine ligand is carried out in toluene, xylene, or other aromatic hydrocarbon solvent; pentane, hexane, or other aliphatic hydrocarbon solvent; methylene chloride or other halogen-containing hydrocarbon solvent; ether, tetrahydrofuran, or other ether solvent; methanol, ethanol, 2-propanol, butanol, benzyl alcohol, or other alcohol solvent; or acetonitrile, N,N-dimethylacetamide (DMA), N,N-dimethylformamide (DMF), N-methylpyrrolidone, dimethyl sulfoxide (DMSO) or other organic solvent containing a heteroatom; at a reaction temperature between −100° C. and 200° C. to obtain a phosphine-ruthenium halide complex.

The reaction of the diamine-phosphine-ruthenium halide complex obtained and an amino ligand is carried out in toluene, xylene, or other aromatic hydrocarbon solvent; pentane, hexane, or other aliphatic hydrocarbon solvent; methylene chloride or other halogen-containing hydrocarbon solvent; ether, tetrahydrofuran, or other ether solvent; methanol, ethanol, 2-propanol, butanol, benzyl alcohol, or other alcohol solvent; or acetonitrile, DMA, DMF, N-methylpyrrolidone, DMSO or other organic solvent containing a heteroatom; at a reaction temperature between −100° C. and 200° C. to obtain a phosphine-ruthenium halide complex.

A ruthenium hydride complex expressed by general formula (1) can be obtained by subsequently hydrogenating the diamine-phosphine-ruthenium halide complex using a metal borohydride. For example, a ruthenium hydride complex expressed by general formula (1) can be obtained by reacting the diamine-phosphine-ruthenium halide complex with a metal borohydride, such as sodium borohydride, potassium borohydride, etc., in toluene, xylene, or other aromatic hydrocarbon solvent; pentane, hexane, or other aliphatic hydrocarbon solvent; methylene chloride or other halogen-containing hydrocarbon solvent; ether, tetrahydrofuran, or other ether solvent; methanol, ethanol, 2-propanol, butanol, benzyl alcohol, or other alcohol solvent; or acetonitrile, DMA, DMF, N-methylpyrrolidone, DMSO or other organic solvent containing a hetero atom; at a reaction temperature between −100° C. and 200° C. A ruthenium hydride complex expressed by general formula (1) can also be obtained by first converting a phosphine-ruthenium halide complex to a phosphine-ruthenium hydride complex and then reacting with a diamine.

When a ruthenium hydride complex expressed by general formula (1) is to be used as a reduction catalyst, though the usage amount thereof will differ according to the reaction vessel and economy, it may be used at molar ratio S/C (S stands for substrate and C stands for catalyst), with respect to a carbonyl compound that is the reaction substrate, of 10 to 5000000 and preferably in the range of 500 to 10000. With a ruthenium hydride complex expressed by general formula (1), a carbonyl compound can be reduced to produce an alcohol compound without the need to add a base for reduction of the carbonyl compound and by mixing with a carbonyl compound under base-free conditions and thereafter applying hydrogen pressure or stirring under the presence of a hydrogen donor. Though this ruthenium hydride complex may be used as a reduction catalyst in isolated form, the ruthenium hydride complex may be as it is used without isolating after preparation, and, for example, the reduction reaction may be carried out in the reaction system used for preparation of the complex.

A suitable solvent may be used as a solvent for preparing an alcohol compound by reduction of a carbonyl compound using a ruthenium hydride complex expressed by general formula (1). Examples include toluene, xylene, or other aromatic hydrocarbon solvent; pentane, hexane, or other aliphatic hydrocarbon solvent; methylene chloride or other halogen-containing hydrocarbon solvent; ether, tetrahydrofuran, or other ether solvent; methanol, ethanol, 2-propanol, butanol, benzyl alcohol, or other alcohol solvent; or acetonitrile, DMA, DMF, N-methylpyrrolidone, DMSO or other organic solvent containing a heteroatom; or a mixed solvent of the above. Here, since the reaction product is an alcohol compound, an alcohol solvent is preferable as the reaction solvent, and among alcohols, a secondary alcohol, such as 2-propanol, is especially preferable. The reduction reaction may also be carried out under solvent-free conditions.

Though a hydrogen pressure of 0.5 atm is sufficient for the reduction reaction as the present catalyst system is extremely high in activity, in view of economy, the hydrogen pressure should be set in the range of 1 to 200 atm and preferably in the range of 3 to 100 atm, and even if the pressure is set to 50 atm or less in view of the economy of the entire process, a high activity can be maintained. Though the reaction temperature is preferably set in the range of 15° C. to 100° C., in view of economy, the reaction may be carried out a temperature near room temperature of 20 to 45° C. The reduction reaction will however proceed even at a low temperature of −30 to 0° C. The reaction time will differ according to the reaction substrate concentration, temperature, pressure, and other reaction conditions, and the reaction will be complete in a few minutes to a few days. In terms of the form of reaction, the reduction reaction may be carried out in batch form or in continuous form.

A complex, among the ruthenium hydride complexes expressed by general formula (1), with which the phosphine ligand is an R form, enables preparation of an optically active alcohol compound by chiral reduction of an asymmetric carbonyl compound in a reaction solvent under the non-presence of a strong base and the presence of hydrogen or hydrogen donating compound. Here, the amine ligand is preferably an optically active diamine. In this case, though the chiral center carbon of the amine ligand may be an R, R form or an S, S form, or both forms may coexist (for example as a racemic mixture), an R, R form or an S, S form is preferable. The use of either an amine ligand of an R, R form or an S, S form is preferably selected in accordance with the type of asymmetric carbonyl compound that is the reaction substrate. That is, depending on the type of asymmetric carbonyl compound more favorable results may be obtained if the amine ligand is of an R, R form or more favorable results may be obtained if the amine ligand is of an S, S form, and it is thus preferable to select the steric structure of the amine ligand in accordance with the reaction substrate. A complex among the ruthenium hydride complexes expressed by general formula (1), with which the phosphine ligand is an S form, also enables preparation of an optically active alcohol compound by chiral reduction of an asymmetric carbonyl compound in a reaction solvent under the non-presence of a strong base and the presence of hydrogen or hydrogen donating compound. Here, the amine ligand is preferably an optically active diamine. In this case, though the chiral center carbon of the amine ligand may be an R, R form or an S, S form, or both forms may coexist (for example as a racemic mixture), an R, R form or an S, S form is preferable. The use of either an amine ligand of an R, R form or an S, S form is preferably selected in accordance with the type of asymmetric carbonyl compound that is the reaction substrate. That is, depending on the type of asymmetric carbonyl compound more favorable results may be obtained if the amine ligand is of an R, R form or more favorable results may be obtained if the amine ligand is of an S, S form, and it is thus preferable to select the steric structure of the amine ligand in accordance with the reaction substrate.

A complex, among the rutheniumhydride complexes expressed by general formula (1), with which the amine ligand is an R, R form, enables preparation of an optically active alcohol compound by chiral reduction of an asymmetric carbonyl compound in a reaction solvent under the non-presence of a strong base and the presence of hydrogen or hydrogen donating compound. Here, though the phosphine ligand may be an R form or an S form, or both forms may coexist (for example as a racemic mixture), an R form or an S form is preferable. The use of either a phosphine ligand of an R form or an S form is preferably selected in accordance with the type of asymmetric carbonyl compound that is the reaction substrate. That is, depending on the type of asymmetric carbonyl compound more favorable results may be obtained if the phosphine ligand is of an R form or more favorable results may be obtained if the phosphine ligand is of an S form, and it is thus preferable to select the steric structure of the phosphine ligand in accordance with the reaction substrate. Further, a complex, among the ruthenium hydride complexes expressed by general formula (1), with which the amine ligand is an S, S form, also enables preparation of an optically active alcohol compound by chiral reduction of an asymmetric carbonyl compound in a reaction solvent under the non-presence of a strong base and the presence of hydrogen or hydrogen donating compound. Here, though the phosphine ligand may be an R form or an S form, or both forms may coexist (for example as a racemic mixture), an R form or an S form is preferable. The use of either an phosphine ligand of an R form or an S form is preferably selected in accordance with the type of asymmetric carbonyl compound that is the reaction substrate. That is, depending on the type of asymmetric carbonyl compound more favorable results may be obtained if the phosphine ligand is of an R form or more favorable results may be obtained if the phosphine ligand is of an S form, and it is thus preferable to select the steric structure of the phosphine ligand in accordance with the reaction substrate.

When a ruthenium hydride complex expressed by general formula (1) is used to prepare an alcohol compound by reduction of an asymmetric carbonyl compound in a reaction solvent under the non-presence of a strong base and the presence of hydrogen or hydrogen donating compound, the asymmetric carbonyl compound may be one that is sensitive to bases. Since a strong base is not made present in this reduction reaction, side reactions besides the carbonyl reduction reaction are less likely to occur even with base-sensitive asymmetric carbonyl compounds. Examples of such base-sensitive asymmetric carbonyl compounds include asymmetric carbonyl compounds, with an ester group, epoxy group, or β-amino group, and α, β-unsaturated ketones, etc. For example, though with an asymmetric carbonyl compound having an ester group, when a reaction is carried out in an alcohol solvent and under the presence of a strong base as in the prior art, there was the problem that an ester exchange reaction, by which the alkoxy part of the ester group is replaced by the solvent alcohol, proceeds as a side reaction, such a problem does not occur with the present invention. Also, in a case where an asymmetric carbonyl compound has an epoxy group, there was the problem that an epoxy ring opening reaction proceeds as a side reaction when a strong base is present as in the prior art, such a problem does not occur with this invention. Furthermore, in a case where an asymmetric carbonyl compound has a β-amino group, there was the problem that elimination of the β-amino group occurs when a strong base is present as in the prior art, such a problem does not occur with this invention. Yet furthermore, in a case of an α, β-unsaturated ketone, such as 3-nonene-2-one, there was the problem that a polymer compound is produced as a side reaction under the presence of a strong base, such a problem does not occur with this invention.

By using a ruthenium hydride complex expressed by general formula (1), one enantiomer, within a mixture of carbonyl compounds consisting of different enantiomers, can be reduced selectively and separated from the other enantiomer, that is, a racemic mixture of carbonyl compounds can be separated in a reaction solvent under the non-presence of a strong base and the presence of hydrogen or hydrogen donating compound. For example, when carbonyl compounds, having a substituent at the α position and with which the carbon at the α position is a chiral carbon, are used as the reaction substrate, since one of the compounds with which the α position is R or S is reduced to an alcohol more rapidly while the other compound remains as a carbonyl compound, optical separation is enabled as a result. Examples of carbonyl compounds, which have a substituent at the α position and with which the carbon at the α position is a chiral carbon, include 2-isopropylcyclohexanone, 2-methylcyclohexanone, 2-isopropylcyclopentanone, 2-isopropylcycloheptanone, 2-ethylcyclohexanone, 2-benzylcyclohexanone, 2-allylcyclohexanone, 2-phenylpropiophenone and other ketones having a hydrocarbon group at the α position, 2-methoxycyclohexanone, 2-ethoxycyclohexanone, 2-isopropyloxycyclohexanone, 2-t-butyloxycyclohexanone, 2-phenoxycyclohexanone, 2-methoxycyclopentanone, 2-methoxycycloheptanone, 2-methoxypropiophenone and other α-alkoxyketones, 2-(dimetylamino)cyclohexanone,2-(methylamino) cyclohexanon, 2-(benzoylmethyl)aminocyclohexanone, 2-(dimethylamino)cyclopentanone, 2-(dimethylamino) cycloheptanone and other α-aminoketones.

DESCRIPTION OF THE PREFERRED EMBODIMENTS

[Measurement Instruments and Devices]

For nuclear magnetic resonance (NMR) measurements, JNM-A400 ($^1$HNMR, 400 MHz; $^{13}$CNMR, 100 MHz; $^3$PNMR, 166 MHz), made by JEOL Ltd., was used. For chemical shifts, δ values were expressed in ppm, tetramethylsilane (TMS) was used as an internal standard substance for $^1$HNMR and $^{13}$CNMR, 10% phosphoric acid in deuterium oxide was used as an external standard for $^{31}$PNMR, and δ=0 was set to the signals of these standards. Coupling constants (J) were expressed in Hz, and with regard to signal splitting modes, a singlet was abbreviated as s, a doublet as d, a triplet as t, a quadruplet as q, a multiplet as m, and a broad line as br. Specific rotations ($[α]_D$) were measured in the indicated solvents and concentrations and using 5 mmφ×5 cm cells in P-1010-GT, made by JASCO Corp. For gas chromatography analysis, measurements by FID using the indicated capillary column and helium pressure were made with 6890,made by Hewlett Packard Inc. For high-performance liquid chromatography analysis, a PU-980 pump, made by JASCO Corp., and a UV-975 UV detector, made by JASCO Corp., were used and measurements were made with the indicated columns, solvents, UV detection wavelengths, and flow rates. Kieselgel 60F254ARt.5715 (0.25 mm thickness), made by Merck & Co., was used for analytical and sampling silica-gel thin-layer chromatography (TLC). Silica Gel 60N (40 to 50 μm), made by Kanto Kagaku Co., Ltd., was used for sampling column chromatography.

Example 1 trans-RuH(η$^1$-BH$_4$)[(R)-tolbinap][(R,R)-dpen] was synthesized. First, trans-RuCl$_2$[(R)-tolbinap][(R,R)-dpen] was synthesized. That is, [RuCl$_2$(benzene)]$_2$ (129 mg; 0.258 mmol) (made by Aldrich Inc.) and (R)-TolBINAP (373 mg; 0.55 mmol) (made by AZmax Co., Ltd.) were weighed and placed in a 50 mL Schlenk reaction tube equipped with a stirrer coated with polytetrafluoroethylene, and after depressurizing the interior of the vessel to eliminate air, argon was introduced. After then adding DMF (9 mL) with a syringe, heating in an oil bath set to 100° C. was performed for 10 minutes under an argon atmosphere. After cooling the reaction solution to room temperature, (R, R)-DPEN (117 mg; 0.55 mmol) (made by Kankyo Kagaku Center Co., Ltd.) was added under an argon gas flow to the reddish-brown RuCl$_2$[(R)-tolbinap](dmf)$_n$ solution, and stirring at 25° C. was performed for 3 hours. To a green-colored crude product obtained by distilling off the DMF under reduced pressure (1 mmHg), methylene chloride (10 mL) was added, and after dissolving as much of a yellow product as possible, a green impurity was removed by filtration. The yellow solution that was obtained by filtration whereafter concentrated to approximately 1 mL and then diethyl ether (5 mL) was added to precipitate solids. The solids obtained were separated by filtration and dried under reduced pressure(1 mmHg)to obtain trans-RuCl$_2$[(R)-tolbinap][(R,R)-dpen] (340 mg; 0.32 mmol; yield: 58%) as a yellow powder. [TolBINAP] and [tolbinap] are abbreviations for 2,2'-bis(di-4-tolylphosphino)-1,1'-binaphthyl, "DMF" and "dmf" are abbreviations for N,N-dimethylformamide, and "DPEN" and "dpen" are abbreviations for 1,2-diphenylethylenediamine.

The abovementioned trans-RuCl$_2$[(R)-tolbinap] [(R,R)-dpen] (106.3 mg; 0.1 mmol) and sodium borohydride (94.6 mg; 2.5 mmol) (made by Nacalai Tesque, Inc.) were then weighed and placed in a 50 mL Schlenk reaction tube equipped with a stirrer coated with polytetrafluoroethylene, and after depressurizing the interior of the vessel to eliminate air, argon was introduced. After then adding a 1:1 volume ratio mixed solvent of benzene/ethanol (4 mL) with a syringe, heating in an oil bath set to 65° C. was performed for 5 minutes under an argon atmosphere. The reaction solution was thereafter stirred for 30 minutes at room temperature. After then drying and solidifying the crude product by distilling off the solvent under reduced pressure (1 mmHg), benzene (6 mL) was added under an argon gas flow to dissolve as much of a yellow product as possible and then the excess sodium borohydride was eliminated by filtration by celite (0.5 g). A yellow filtrate thus obtained was concentrated to approximately 1 ml by depressurization (1 mm Hg) and hexane (6 mL) was then added under an argon gas flow. Yellow solids thus precipitated were separated by filtration through a glass filter and dried under reduced pressure (1 mmHg) to obtain trans-RuH(η$^1$-BH$_4$)[(R)-tolbinap] [(R,R)-dpen] (76.0 mg; yield: 70%; see formula (3) below) as a yellow powder. Decomposition temperature: 164° C.; $^1$HNMR(400 MHZ, C$_6$D$_6$) δ−13.60(t, 1, J=22.4 Hz, RuH), −0.40(brs, 4, BH$_4$), 1.45(s, 3, CH$_3$), 1.55(s, 3, CH$_3$), 1.62(s, 3, CH$_3$), 1.63(s, 3, CH$_3$), 1.95(dd, 1, J=7.2 and 8.4 Hz, NHH), 2.38(d, 1, J=8.2 Hz, NHH) ,3.65(dd, 1, J=7.9 and 11.2 Hz, CHNH$_2$), 3.82–3.88(m, 2, 2 NHH), 4.00(ddd, 1, J=7.9, 8.4 and 11.6 Hz, CHNH$_2$), 6.13–8.12(m, 38, aromatics) ;$^{31}$PNMR(161.7 MHz, C$_6$D$_6$) δ71.2(d, J=41.4 Hz), 75.2(d, J=41.4 Hz);IR(toluene)2316(s), 1862(s), 1092 (s), 1080(s)cm$^{-1}$; ESI-MS m/z1007.26([M−H]+), theoretical value (C$_{62}$H$_{60}$BN$_2$P$_2$Ru): 1007.34. The powder obtained was then recrystallized from a THF/hexane mixed solvent of a volume ratio of approximately 1:5 to obtain yellow prismatic crystals, and these were used for X-ray crystallography.

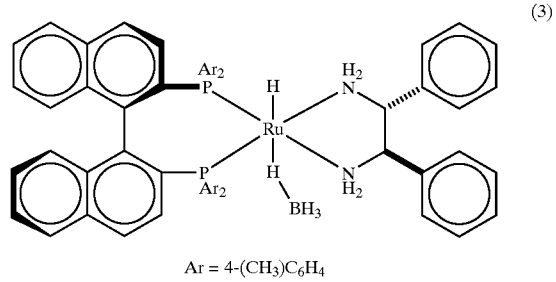

(3)

Ar = 4-(CH$_3$)C$_6$H$_4$

Example 2 trans-RuH(η$^1$-BH$_4$)[(s)-xylbinap][(S,S)-dpen] was synthesized. First, trans-RuCl$_2$[(S)-xylbinap][(S,S)-dpen] was synthesized. That is, [RuCl$_2$(benzene)]$_2$ (62.5 mg; 0.125 mmol) (made by Aldrich Inc.) and (R)-XylBINAP (183.5 mg; 0.25 mmol) were weighed and placed in a 75 mL Schlenk reaction tube equipped with a stirrer coated with polytetrafluoroethylene, and after depressurizing the interior of the vessel to eliminate air, argon was introduced. After then adding DMF (3 mL) with a syringe, heating in an oil bath set to 100° C. was performed for 10 minutes under an argon atmosphere. After cooling the reaction solution to room temperature, DMF was distilled off under reduced pressure(1 mmHg). (S, S)-DPEN (53.0 mg; 0.25 mmol) (made by Kankyo Kagaku Center Co., Ltd.) and methylene chloride (3 mL) were then added under an argon gas flow to the reddish-brown RuCl$_2$[(S)-xylbinap] (dmf)$_n$ solution thus obtained and stirring at 25° C. was performed for 1 hour. A green-colored crude product obtained by distilling off the methylene chloride under reduced pressure (1 mmHg) was dissolved in a 1:1 volume ratio methylene chloride/diethyl ether mixed solvent (2 mL) and this was passed through a column packed with silica gel (5 g) using a 1:1 volume ratio diethyl ether-hexane solution as an eluate to remove impurities. A yellow solution obtained as a precursor was then concentrated until a complex precipitated and solids were separated by filtration and dried under reduced pressure (1 mmHg) to obtain trans-RuCl$_2$[(S)-xylbinap][(S,S)-dpen] (214.8 mg; 0.192 mmol; yield: 77%) as a yellow powder. [XylBINAP] and [xylbinap] are abbreviations for 2,2'-bis(di-3,5-xylylphosphino)-1,1'-binaphthyl.

The abovementioned trans-RuCl$_2$[(S)-xylbinap] [(S,S)-dpen] (89.5 mg; 0.08 mmol) and sodium borohydride (75.6 mg; 2.0 mmol) (made by Nacalai Tesque, Inc.) were then weighed and placed in a 20 mL Schlenk reaction tube equipped with a stirrer coated with polytetrafluoroethylene, and after depressurizing the interior of the vessel to eliminate air, argon was introduced. After then adding a 1:1 volume ratio mixed solvent of benzene/ethanol (6 mL) with a syringe, heating in an oil bath set to 65° C. was performed for 5 minutes under an argon atmosphere. The reaction solution was thereafter stirred for 30 minutes at room temperature. After then drying and solidifying the crude product by distilling off the solvent under reduced pressure (1 mmHg), hexane (5 mL) was added under an argon gas flow to dissolve as much of a yellow product as possible and then the excess sodium borohydride was eliminated by filtration by celite (0.5 g). A yellow filtrate thus obtained was concentrated to approximately 1 ml by depressurization (1 mm Hg) and yellow solids thus precipitated were separated by filtration through a glass filter and dried under reduced pressure (1 mmHg) to obtain trans-RuH($\eta^1$-BH$_4$)[(S)-xylbinap][(S,S)-dpen] (38.3 mg; yield: 45%; see formula (4) below) as a yellow powder. Decomposition temperature: 220° C.; $^1$HNMR(400 MHz, C$_6$D$_6$) δ–13.67(t, 1, J=23.2 Hz, RuH), –0.48(brs, 4, BH$_4$), 1.59(brs, 12, 4 CH$_3$), 1.78(s, 6, 2CH$_3$), 2.00(s, 6, 2CH$_3$), 2.28–2.35(m, 2, 2NHH), 3.62–3.67 (m, 1, CHNH$_2$), 3.76–3.81(m, 2,2CHNH$_2$), 4.09 (dd, 1, J=9.6 and 18.2 Hz, CHNH$_2$), 5.77–8.38(m, 34, aromatics); $^{31}$PNMR(161.7 MHz, C$_6$D$_6$) δ73.1(d, J=41.4 Hz), 76.8(d, J=41.4 Hz); IR(toluene)2319(s), 1850(s), 1125(s)cm$^{-1}$; ESI-MS m/z1063.33([M–H]+), theoretical value (C$_{66}$H$_{68}$BN$_2$P$_2$Ru): 1063.40.

(4)

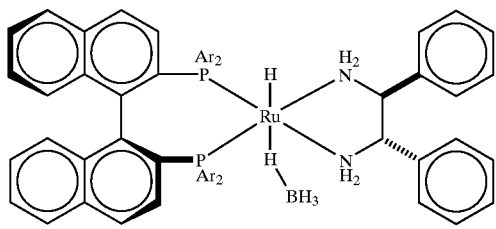

Ar = 3,5-(CH$_3$)$_2$C$_6$H$_3$

Example 3 trans-RuH($\eta^1$-BH$_4$)[(S)-xylbinap][(R,R)-dpen] was synthesized. First, trans-RuCl$_2$[(S)-xylbinap][(R,R)-dpen] was synthesized. That is, [RuCl$_2$(benzene)]$_2$ (25.0 mg; 0.05 mmol) (made by Aldrich Inc.) and (R)-XylBINAP (73.4 mg; 0.1 mmol) were weighed and placed in a 75 mL Schlenk reaction tube equipped with a stirrer coated with polytetrafluoroethylene, and after depressurizing the interior of the vessel to eliminate air, argon was introduced. After then adding DMF (2 mL) with a syringe, heating in an oil bath set to 100° C. was performed for 10 minutes under an argon atmosphere. After cooling the reaction solution to room temperature, DMF was distilled off under reduced pressure 1 mmHg). (R, R)-DPEN (53.0 mg; 0.25 mmol) and methylene chloride (1.5 mL) were then added under an argon gas flow to the reddish-brown RuCl$_2$[(S)-xylbinap](dmf)$_n$ solution thus obtained and stirring at 25° C. was performed for 1 hour. A green-colored crude product obtained by distilling off the methylene chloride under reduced pressure (1 mmHg) was dissolved in a 1:1 volume ratio methylene chloride/diethyl ether mixed solvent (2 mL) and this was passed through a column packed with silica gel (5 g) using a 1:1 volume ratio diethyl ether-hexane solution as an eluate to remove impurities. A yellow solution obtained as a precursor was then concentrated until a complex precipitated and solids were separated by filtration and dried under reduced pressure(1 mmHg) to obtain trans-RuCl$_2$[(S)-xylbinap][(R,R)-dpen] (74.9 mg; 0.067 mmol; yield: 67%) as a yellow powder.

The abovementioned trans-RuCl$_2$[(S)-xylbinap] [(R,R)-dpen] (67.1 mg; 0.06 mmol) and sodium borohydride (56.7 mg; 1.5 mmol) were then weighed and placed in a 20 mL Schlenk reaction tube equipped with a stirrer coated with polytetrafluoroethylene, and after depressurizing the interior of the vessel to eliminate air, argon was introduced. After then adding a 1:1 volume ratio mixed solvent of benzene/ethanol (4 mL) with a syringe, heating in an oil bath set to 65° C. was performed for 5 minutes under an argon atmosphere. The reaction solution was thereafter stirred for 30 minutes at room temperature. After then drying and solidifying the crude product by distilling off the solvent under reduced pressure (1 mmHg), hexane (5 mL) was added under an argon gas flow to dissolve as much of a yellow product as possible and then the excess sodium borohydride was eliminated by filtration by celite (0.5 g). A yellow filtrate thus obtained was concentrated to approximately 1 ml by depressurization (1 mm Hg) and yellow solids thus precipitated were separated by filtration through a glass filter and dried under reduced pressure (1 mmHg) to obtain trans-RuH ($\eta^1$-BH$_4$)[(S)-xylbinap][(R,R)-dpen] (40.5 mg; yield: 63%; see formula (5) below) as a yellow powder. Decomposition temperature: 218° C.; $^1$HNMR(400 MHz, C$_6$D$_6$) δ–13.60 (dd, 1, J=22.0 and 24.6 Hz, RuH), –0.48(brs, 4, BH$_4$), 1.58(brs, 12, 4CH$_3$), 1.71(s, 6, 2CH$_3$), 1.96(s, 6, 2CH$_3$), 2.08(d, 1, J=9.2 Hz, NHH), 2.66–2.70(m, 1, NHH), 3.11(dd, 1, J=9.2 and 9.2 Hz, NHH),3.93–3.99(m, 1, CHNH$_2$), 4.24–4.31(m, 1, CHNH$_2$), 4.88(dd, 1, J=10.4 and 10.4 Hz, NHH), 5.78–8.39(m, 34, aromatics); $^{31}$PNMR(161.7 MHz, C$_6$D$_6$) δ73.2(d, J=41.6 Hz), 76.0(d, J=41.6 Hz); IR(toluene) 2322(s), 1850(s), 1125(s)cm$^{-1}$; ESI-MS m/z1063.35( [M–H]+), theoretical value (C$_{66}$H$_{68}$BN$_2$P$_2$Ru): 1063.40.

(5)

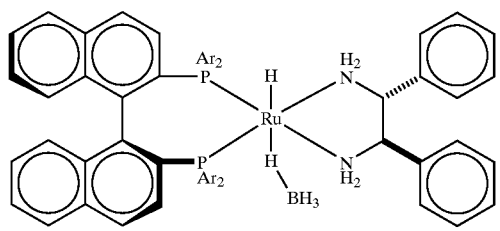

Ar = 3,5-(CH$_3$)$_2$C$_6$H$_3$

Example 4

Chiral hydrogenation of acetophenone was carried out (generally-used procedures; see formula (6) below). The (S,SS)-ruthenium hydride complex (1.5 mg; 0.00125 mmol) synthesized in Example 2 was weighed and placed in a 100 mL glass autoclave equipped with a stirrer coated with polytetrafluoroethylene, and after depressurizing the interior of the vessel to eliminate air, argon was introduced. Acetophenone (600 mg; 5.0 mmol) (made by Nacalai Tesque, Inc.) and 2-propanol (2.5 mL), both of which had been deaerated by argon bubbling in advance, were then added into the vessel by means of a syringe and under an argon gas flow. The procedure of performing pressure reduction and argon introduction while stirring the solution obtained was then repeated 5 times for deaeration. A hydrogen tank was then connected to the autoclave using a hydrogen introduction tube and the replacement of the air inside the introduction tube with hydrogen at 2 atmospheres was performed 5 times. The pressure inside the autoclave was then adjusted to 5 atmospheres and then hydrogen was released carefully until the pressure dropped to 1 atmosphere. After repeating this procedure 10 times, the hydrogen pressure was adjusted to 8 atmospheres and vigorous stirring at 25° C. was performed for 12 hours. After completion of reaction, the solution obtained was concentrated by depressurization. The crude product was then subject to simple distillation under reduced pressure (1 mmHg) to obtain (R)-1-phenylethanol (582 mg; 4.75 mmol; yield: 95%) at an ee of 99% as a colorless oily substance. Both conversion rate and enantiomeric excess were 99% in accordance with GC analysis: GC (column: Chirasil-DEX CB; inner diameter (df): 0.25 mm; size: 0.32 mm×25 m; made by Chromopack, Inc.; column temperature: 105° C.; injection and detection temperature: 200° C.; helium pressure: 41 kPa; retention time ($t_R$) of (R)-1-phenylethanol: 21.7 minutes (99.56%); $t_R$ of (S)-1-phenylethanol: 23.5 minutes (0.43%); $t_R$ of acetophenone: 9.5 minutes (0.01%)); $^1$HNMR (400 MHz, CDCl$_3$)δ1.50 (d, 3, J=6.6 Hz, CH$_3$), 4.90 (dq, 1, J=3.3 and 6.6 Hz, CHOH), 7.21–7.41 (m, 5, aromatics); $[\alpha]^{28}_D$: +51.8° (c: 0.984; CH$_2$Cl$_2$); absolute structure: R; literature value: $[\alpha]^{23}_D$+48.6° (c: 0.9–1.1; CH$_2$Cl$_2$), 96% ee (R).

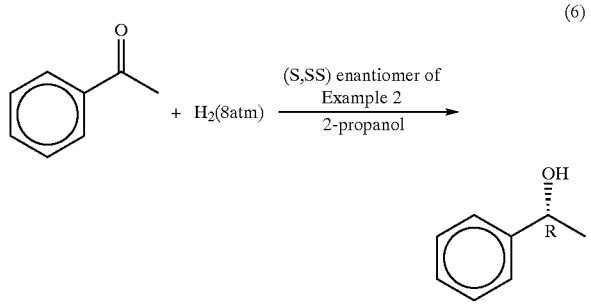

Example 5

Chiral hydrogenation of acetophenone was carried out (see formula (7) below). That is, a reaction was carried out in accordance with the procedures of Example 4 using the (S,SS)-ruthenium hydride complex (1.5 mg; 0.00125 mmol) synthesized in Example 2 and using acetophenone (150 mg; 1.25 mmol) as the substrate and 2-propanol (1.5 mL) as the solvent. However, the hydrogen pressure was set to 1 atmosphere, the reaction temperature was set to 25° C., and the reaction time was set to 12 hours. As a result, (R)-1-phenylethanol was obtained at a conversion rate of 99%, isolation yield of 95% (293 mg; 1.19 mmol), and enantiomeric excess of 97%.

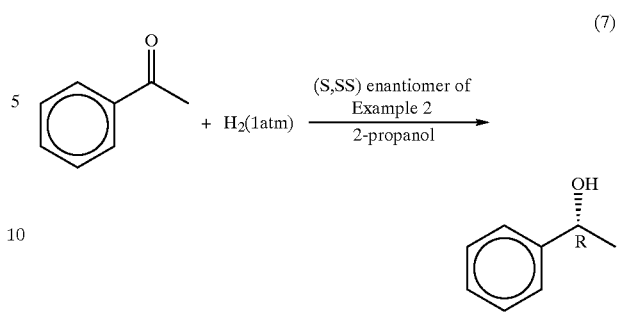

Example 6

Chiral hydrogenation of acetophenone was carried out (see formula (8) below). That is, a reaction was carried out in accordance with the procedures of Example 4 using the (R,RR)-ruthenium hydride complex (45.3 mg; 0.0425 mmol) synthesized in Example 1 and using acetophenone (102.1 g; 0.85 mol) as the substrate and 2-propanol (100 mL) as the solvent. However, the hydrogen pressure was set to 10 atmosphere, the reaction temperature was set to 22~41° C., and the reaction time was set to 14 hours. As a result, (S)-1-phenylethanol was obtained at a conversion rate of 99.8%, isolation yield of 97% (100.7 g; 0.82 mol), and enantiomeric excess of 81%.

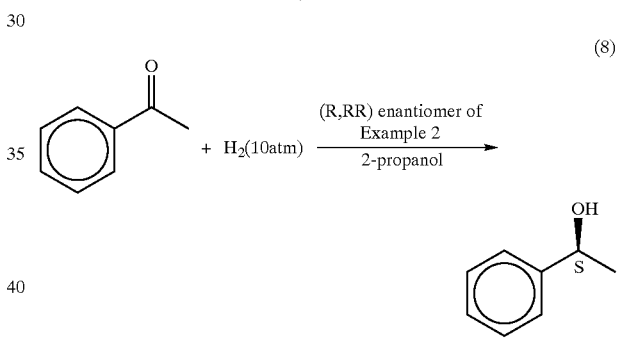

Example 7

Chiral hydrogenation of ethyl 4-acetylbenzoate was carried out (see formula (9) below). That is, a reaction was carried out in accordance with the procedures of Example 4 using the (S,SS)-ruthenium hydride complex (1.5 mg; 0.00125 mmol) synthesized in Example 2 and using ethyl 4-acetylbenzoate (961 mg; 5.00 mmol) (Wako.Co.,Ltd.) as the substrate and 2-propanol (5 mL) as the solvent. However, the hydrogen pressure was set to 8 atmosphere, the reaction temperature was set to 25° C., and the reaction time was set to 15 hours. As a result, ethyl (R)-4-(1-hydroxyethyl) benzoate was obtained at a conversion rate of 100%, isolation yield of 98% (951 mg; 4.9 mmol), and enantiomeric excess of 99%. GC (column: Chirasil-DEXCB; column temperature: 150° C.; injection and detection temperature: 250° C.; helium pressure: 49 kPa; $t_R$ of ethyl (R)-4-(1-hydroxyethyl) benzoate : 32.2 minutes (99.4%); $t_R$ of ethyl (S)-4-(1-hydroxyethyl) benzoate: 35.1 minutes (0.6%)); $t_R$ of ethyl 4-acetylbenzoate 35.5 minutes (0%); $[\alpha]^{26}_D$: +32.0° (c:0.912; CH$_3$OH); absolute structure: R; literature value: $[\alpha]^{21}_D$+32.6° (c:0.873; CH$_3$OH), 98.6% ee (R).

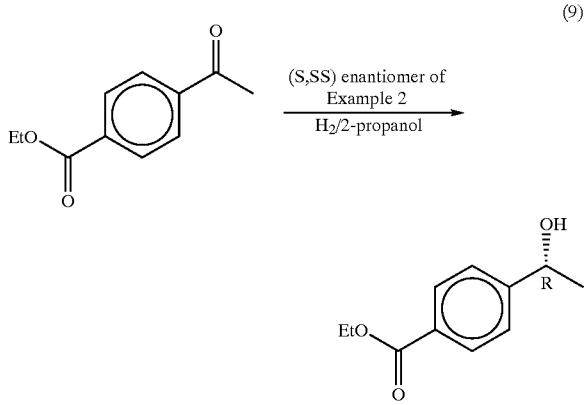

Example 8

Chiral hydrogenation of (R)-acetone glyceryl 4-acetylbenzoate was carried out(see formula (10) below). That is, a reaction was carried out in accordance with the procedures of Example 4 using the (S,SS)-ruthenium hydride complex (1.5 mg; 0.00125 mmol) synthesized in Example2 and using (R)-acetone glyceryl 4-acetylbenzoate (696 mg; 2.5 mmol) as the substrate and 2-propanol (2.5 mL) as the solvent. However, the hydrogen pressure was set to 8 atmosphere, the reaction temperature was set to 25° C., and the reaction time was set to 16 hours. As a result, (R)-acetone glyceryl (R)-4-(1-hydroxyethyl)benzoate was obtained at a conversion rate of 100%, isolation yield of 98% (686 mg; 2.45 mmol), and enantiomeric excess of 99%. HPLC (column: CHIRALCEL OB-H; size: 4.6 mm×250 mm; made by Daicel Chemical Industries Ltd.; solvent: 9:1 hexane/2-propanol; temperature: 30° C.; UV wavelength: 254 nm; flow rate: 0.5 ml/minute; $t_R$ of (R)-acetone glyceryl (R)-4-(1-hydroxyethyl)benzoate: 24.6 minutes (98.3%); $t_R$ of S,R alcohol: 18.9 minutes (1.7%)); $[\alpha]^{29}_D$: +34.2° (c:1.085; CHCl$_3$); absolute structure: R. The absolute structure was determined by GC analysis after conversion to the corresponding ethyl ester.

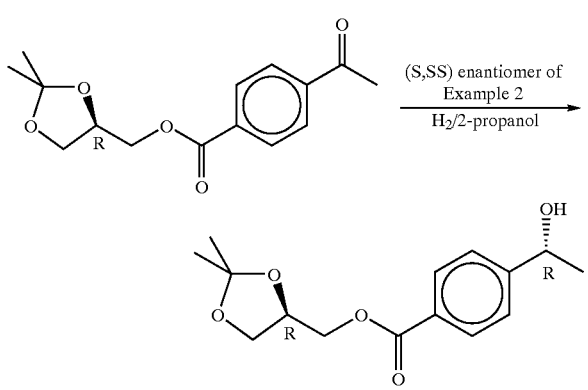

Example 9

Chiral hydrogenation of methyl 7-oxo-7-phenylheptanoate was carried out (see formula (11) below). That is, a reaction was carried out in accordance with the procedures of Example 4 using the (S, SS)-ruthenium hydride complex (1.5 mg; 0.00125 mmol) synthesized in Example 2 and using methyl 7-oxo-7-phenylheptanoate (587 mg; 2.5 mmol) as the substrate and 2-propanol (2.5 mL) as the solvent. However, the hydrogen pressure was set to 8 atmosphere, the reaction temperature was set to 25° C., and the reaction time was set to 12 hours. As a result, methyl (R)-7-hydroxy-7-phenylheptanoate was obtained at a conversion rate of 100%, isolation yield of 98% (588 mg; 2.48 mmol), and enantiomeric excess of 95%. The enantiomeric excess was determined by HPLC analysis of the corresponding benzoic acid ester. HPLC (column: CHIRALPAC AD: size: 4.6 mm×250 mm; made by Daicel Chemical Industries Ltd.; solvent: hexane/2-propanol=19:1; temperature: 30° C.; UV wavelength: 254 nm; flow rate: 0.5 ml/minute; $t_R$ of methyl (R)-7-benzoyloxy-7-phenylheptanoate: 20.8 minutes (97.6%); $t_R$ of the Sisomer:25.9 minutes(2.4%)); $[\alpha]^{28}_D$+ 29.1° (c:1.09;CHCl$_3$); absolute structure: R. The absolute structure was determined from the value of the angle of rotation of 1-phenylheptanol obtained by conversion.

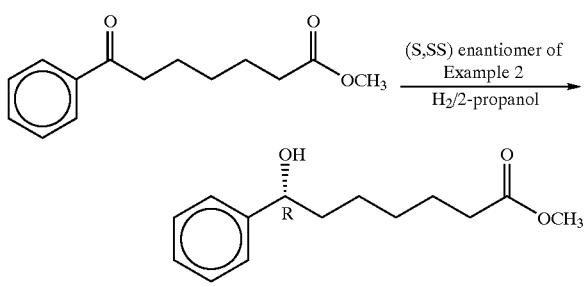

Example 10

Chiral hydrogenation of (R)-glycidyl 3-acetylphenyl ether was carried out (see formula (12) below). That is, a reaction was carried out in accordance with the procedures of Example 4 using the (S,SS)-ruthenium hydride complex (1.5 mg; 0.00125 mmol) synthesized in Example 2 and using (R)-glycidyl 3-acetylphenyl ether (481 mg; 2.5 mmol) as the substrate and 2-propanol (2.5 mL) as the solvent. However, the hydrogen pressure was set to 8 atmosphere, the reaction temperature was set to 25° C., and the reaction time was set to 14 hours. As a result, one of the stereoisomers of (R)-glycidyl 3-(1-hydroxyethyl)phenyl ether was obtained at a conversion rate of 99%, isolation yield of 98% (475 mg; 2.45 mmol), and enantiomeric excess of 99%. GC (column: Chirasil-DEX CB; column temperature: 135° C.; injection and detection temperature: 250° C.; helium pressure: 60 kPa; $t_R$ of (R)-glycidyl (R) or (S)-3-(1-hydroxyethyl)phenyl ether: 94.9 minutes (98.6%); $t_R$ of the stereoisomers: 109.6 minutes (0.5%); $t_R$ of (R)-glycidyl 3-acetylphenyl ether: 46.5 minutes (0.9%); $[\alpha]^{29}_D$: +32.0° (c: 1.36; CHCl$_3$); The absolute structure was not determined.

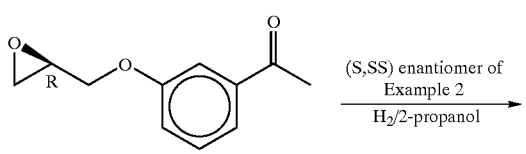

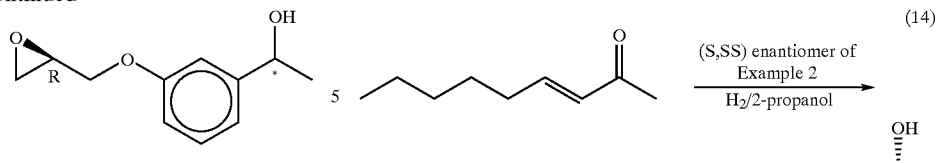

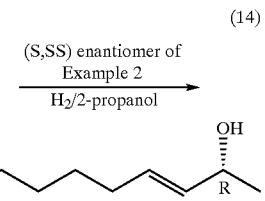

Example 11

Chiral hydrogenation of 3-(dimethylamino) propiophenone was carried out (see formula (13) below). That is, a reaction was carried out in accordance with the procedures of Example 4 using the (S,SS)-ruthenium hydride complex synthesized in Example 2 and using 3-(dimethylamino)propiophenone(886 mg; 5.0 mmol) as the substrate and 2-propanol (5 mL) as the solvent. However, the hydrogen pressure was set to 8 atmosphere, the reaction temperature was set to 250° C., and the reaction time was set to 12 hours. As a result, (R)-1-phenyl-3-(dimethylamino) propane-1-ol was obtained at a conversion rate of 100%, isolation yield of 89% (796 mg; 4.45 mmol), and enantiomeric excess of 97%. HPLC (column: CHIRALCEL OD; size: 4.6 mm×250 mm; made by Daicel Chemical Industries Ltd.; solvent: 9:1 hexane/2-propanol; temperature: 30° C.; UV wavelength: 254 nm; flow rate: 0.5 ml/minute; $t_R$ of (R)-1-phenyl-3-(dimethylamino)propane-1-ol: 14.4 minutes (98.4%); $t_R$ of S alcohol: 20.4 minutes (1.6%)); $[\alpha]^{26}_D$+ 31.8° (c: 1.67; $CH_3OH$); absolute structure: R; literature value: $[\alpha]_D$+27.6° (c:1.61; $CH_3OH$),(R).

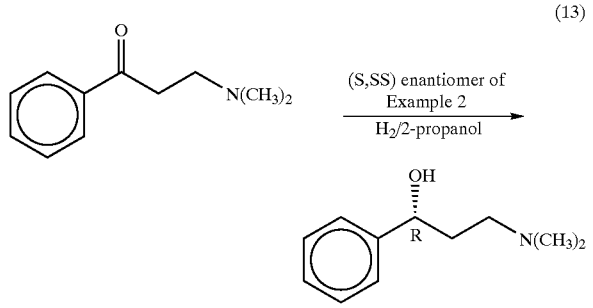

Example 12

Chiral hydrogenation of (E)-3-nonene-2-one was carried out(see formula (14) below). That is, a reaction was carried out in accordance with the procedures of Example 4 using the (S,SS)-ruthenium hydride complex (1.5 mg; 0.00125 mmol) synthesized in Example 2 and using (E)-3-nonene-2-one (701 mg; 5.0 mmol) (made by Tokyo Kasei Kogyo Co., Ltd.)as the substrate and 2-propanol (2.5 mL) as the solvent. However, the hydrogen pressure was set to 8 atmosphere, the reaction temperature was set to 25° C., and the reaction time was set to 16 hours. As a result, (E)-3-nonene-2-ol was obtained at a GC yield of 95%, isolation yield of 93% (668 mg; 4.65 mmol), and enantiomeric excess of 99%. GC (column: Chirasil-DEX CB; column temperature: 65° C.; injection and detection temperature: 200° C.; helium pressure: 41 kPa; $t_R$ of (R)-(E)-3-nonene-2-ol: 70.5 minutes(99.6%); $t_R$ of (S)-(E)-3-nonene-2-ol:80.7 minutes (0.4%)); $[\alpha]^{26}_D$+21.16° (c:1.042; $CHCl_3$); absolute structure: R; literature value: $[\alpha]^{25}_D$+10.68° (c:1.03; $CHCl_3$), 97% ee (R).

Example 13

Kinetic resolution of racemic 2-isopropylcyclohexanones was carried out(generally-used procedures; see formula (15) below). The (S,RR)-ruthenium hydride complex (1.5 mg; 0.00125 mmol) synthesized in Example 3 was weighed and placed in a 100 mL glass autoclave equipped with a stirrer coated with polytetrafluoroethylene, and after depressurizing the interior of the vessel to eliminate air, argon was introduced. 2-isopropylcyclohexanones (351 mg; 2.5 mmol) and 2-propanol (2.5 mL), both of which had been deaerated by argon bubbling in advance, were then added into the vessel by means of a syringe and under an argon gas flow. The procedure of performing pressure reduction and argon introduction while stirring the solution obtained was then repeated 5 times for deaeration. A hydrogen tank was then connected to the autoclave using a hydrogen introduction tube and the replacement of the air inside the introduction tube with hydrogen at 2 atmospheres was performed 5 times. The pressure inside the autoclave was then adjusted to 5 atmospheres and then hydrogen was released carefully until the pressure dropped to 1 atmosphere. After repeating this procedure 10 times, the hydrogen pressure was adjusted to 8 atmospheres and then vigorous stirring was performed until the hydrogen pressure decreased to approximately 0.4 atmospheres as measured by a manometer (2 hours). After then releasing the hydrogen carefully, the solution obtained was concentrated by depressurization. The crude product was then subject to silica gel chromatography (silica gel: 18 g; solvent: 1:8 ethyl acetate/hexane), and (S)-2-isopropylcyclohexanone (154 mg; 1.10 mmol; yield: 44%; enantiomeric excess 91%) was obtained as a first fraction and (1R, 2R)-2-isopropylcyclohexanol (168 mg; 1.20 mmol; yield: 48%; enantiomeric excess 85%) was obtained as a second fraction. GC (column: Chirasil-DEXCB; column temperature: after setting at 70° C. for 70 min, raised to 100° C. at a rate of 5° C./min; injection and detection temperature: 200° C.; helium pressure: 41 kPa; $t_R$ of (R)-2- isopropylcyclohexanones: 64.3 minutes (2.0%); $t_R$ of S ketone: 65.8 minutes (44.9%); $t_R$ of (1R, 2R)-2-isopropylcyclohexanol: 90.7 minutes (49.1%); $t_R$ of 1S, 2S alcohol: 89.4 minutes (4.0%). specific rotation of ketone: $[\alpha]^{27}_D$: −71.1° (c:0.93; $CHCl_3$); the absolute structure was determined from the specific rotation of the K-selectride reduction product of (S)-2-isopropylcyclohexanone: $[\alpha]^{25}_D$: +18.9° (c:0.35; $CHCl_3$); absolute structure: 1S, 2S. specific rotation of alcohol: $[\alpha]^{26}_D$: −19.2° (c:1.085; $CHCl_3$); absolute structure: 1R, 2R; literature value: $[\alpha]^{25}_D$−18.0° (c:1.0; $CHCl_3$), 93% ee (1R, 2R).

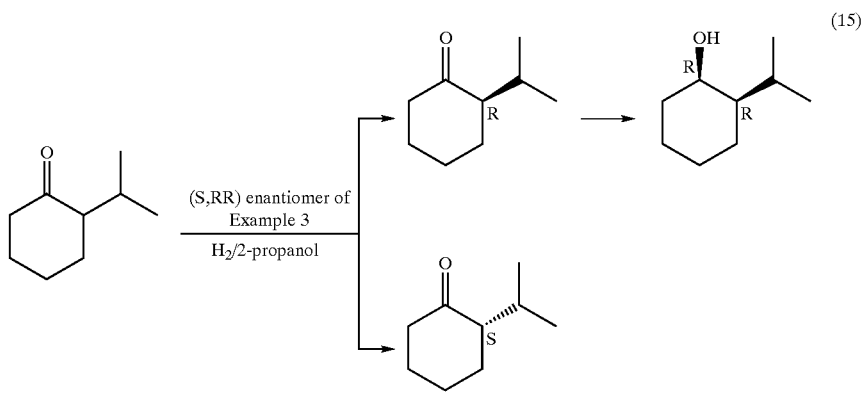

(15)

Example 14

Kinetic resolution of racemic 2-methoxycyclohexanone was carried out (see formula (16) below) That is, a reaction was carried out in accordance with the procedures of Example 13 using the (S,SS)-ruthenium hydride complex (1.5 mg; 0.00125 mmol) synthesized in Example 2 and using 2-methoxycyclohexanone (320 mg; 2.5 mmol) (made by Tokyo Kasei Kogyo Co., Ltd. )as the substrate and 2-propanol (2.5 mL) as the solvent. However, the hydrogen pressure was set to 8 atmosphere, the reaction temperature was set to 25° C., and the reaction time was set to 1 hours. As a result, (R)-2-methoxycyclohexanone was obtained at isolation yield of 42% (134 mg; 1.05 mmol), (1R, 2S)-2-methoxycyclohexanol was obtained at isolation yield of 50% (164 mg; 1.25 mmol and enantiomeric excess of 91%). GC (column: Chirasil-DEX CB; column temperature:90° C.; injection and detection temperature: 200° C.; helium pressure: 25 kPa; $t_R$ of (1R,2S)-2-methoxycyclohexanol: 37.6 minutes(50.8%); $t_R$ of 1S, 2S alcohol: 36.5 minutes (2.5%); $t_R$ of 2-methoxycyclohexanone:27.0 minutes (46.7%)). enantiomeric excess of (R)-2-methoxycyclohexanone:94% : HPLC (column: CHIRAL-CEL OB-H; solvent: 200:1 hexane/2-propanol; temperature: 30° C.; UV wavelength: 290 nm; flow rate: 1.0 ml/minute; $t_R$ of (R)-2-methoxycyclohexanone: 20.9 minutes (97.2%); $t_R$ of Sketone: 17.0 minutes (2.8%). specific rotation of ketone: $[\alpha]^{29}_D+98.8°$ (c:2.61; $CH_2Cl_2$); absolute structure: R; literature value: $[\alpha]^{22}_D-112.4°$ (c:2.08;$CH_2Cl_2$),>99%ee (S). specific rotation of alcohol: $[\alpha]^{29}_D+14.9°$ (c:1.026; $CH_2Cl_2$); absolute structure: 1R, 2S: the absolute structure was determined by HPLC analysis of the product of oxidation of (1R, 2S)-2-methoxycyclohexanol.

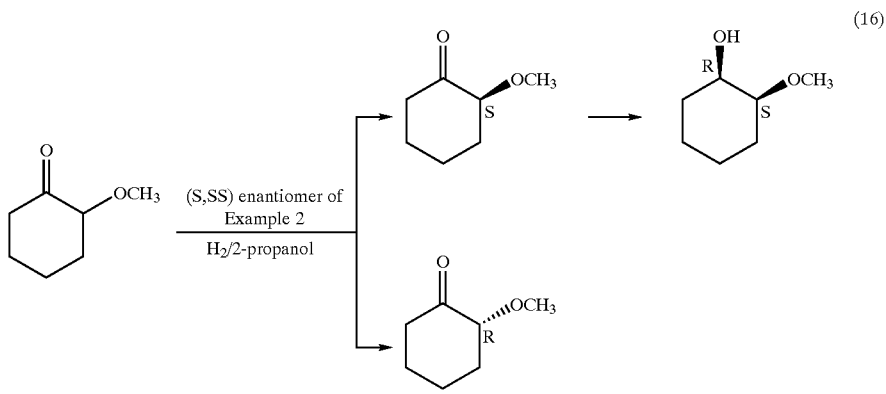

(16)

Example 15

First, a ruthenium chloride complex was prepared. That is, [$RuCl_2$(benzene)]$_2$(407 mg;0.814 mmol) and (S)-XylBINAP (1.20 g; 1.63 mmol) were weighed and placed in a 50 mL Schlenk reaction tube equipped with a stirrer coated with polytetrafluoroethylene, and after depressurizing the interior of the vessel to eliminate air, argon was introduced. After then adding DMF (12 mL) with a syringe, heating in an oil bath set to 100° C. was performed for 10 minutes under an argon atmosphere. After cooling the reaction solution to room temperature,(S)-1,1-di(4-anisyl)-2-isopropylethylenediamine [(S)-DAIPEN] (512 mg; 1.63 mmol) (made by Kanto Kagaku Co., Ltd.) was added under argon gas flow to the reddish-brown $RuCl_2$[(S)-xylbinap](dmf)$_n$ solution, and stirring at 25° C. was performed for 6 hours. To the black crude product that was obtained by distilling off DMF under reduced pressure (1 mmHg), diethyl ether (40 mL) was added to dissolve a yellow product as much as possible and the resulting solution was then passed through a column packed with silica gel (3.5 g) to remove impurities. The yellow solution that was obtained as a precursor was then concentrated to approximately 2 mL and then hexane (2 mL) was added to precipitate solids. The solids obtained were separated by filtration and dried under reduced pressure (1 mmHg) to obtain trans-$RuCl_2$[(S)-xylbinap][(S)-daipen] (1.25 g; 1.023 mmol; yield: 53%) as a yellow powder.

A ruthenium hydride complex was then prepared using the ruthenium chloride thus obtained, and this complex was used without isolation to carry out chiral hydrogenation of acetophenone. That is, trans-RuCl$_2$[(S)-xylbinap][(S)-daipen] (1.5 mg; 0.00125 mmol) and sodium borohydride (0.9 mg; 0.025 mmol) were weighed and placed in a 100 mL glass autoclave equipped with a stirrer coated with polytetrafluoroethylene, and after depressurizing the interior of the vessel to eliminate air, argon was introduced. 2-propanol (1 mL), which had been deaerated by argon bubbling in advance, was then added into the vessel by means of a syringe and under an argon gas flow. The procedure of performing pressure reduction and argon introduction while stirring the solution obtained was then repeated 5 times for deaeration, and then upon immersing in an oil bath for 5 minutes at 65° C., vigorous stirring was subsequently performed for 30 minutes at room temperature. Acetophenone (600 mg; 5.0 mmol) and 2-propanol (1.5 mL) were then added into the vessel by means of a syringe and under an argon gas flow. The procedure of performing pressure reduction and argon introduction while stirring the solution obtained was then repeated 5 times for deaeration. A hydrogen tank was then connected to the autoclave using a hydrogen introduction tube and the replacement of the air inside the introduction tube with hydrogen at 2 atmospheres was performed 5 times. The pressure inside the autoclave was then adjusted to 5 atmospheres and then hydrogen was released carefully until the pressure dropped to 1 atmosphere. After repeating this procedure 10 times, the hydrogen pressure was adjusted to 8 atmospheres and vigorous stirring at 25° C. was performed for 12 hours. After completion of reaction, by concentrating the solution obtained by depressurization and subjecting the same to simple distillation under reduced pressure (1 mmHg), (R)-1-phenylethanol (579 mg; 4.75 mmol; yield: 95%; enantiomeric excess: 98%) was obtained.

What is claimed is:

1. A ruthenium hydride complex expressed by the following general formula (1):

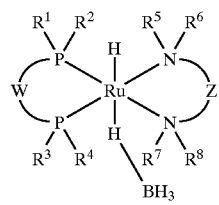

(1)

(wherein for R$^1$R$^2$P—W—PR$^3$R$^4$, W is a binaphthyl group, which is bonded to phosphorus atoms at positions 2 and 2' and may have one or more substituents at any of the other positions, each of R$^1$ to R$^4$ is the same or different hydrocarbon group that may or may not have one or more substituents, R$^1$ and R$^2$ may together form a carbon chain ring that may have one or more substituents, R$^3$ and R$^4$ may together form a carbon chain ring that may have one or more substituents, each of R$^5$ to R$^8$ is the same or different hydrocarbon group that may or may not have one or more substituents, Z is a hydrocarbon group that may or may not have one or more substituents, and each of the ligands of Ru may be positioned in any manner).

2. The ruthenium hydride complex as set forth in claim 1, wherein the amine ligand is an optically active diamine.

3. The ruthenium hydride complex as set forth in claim 1, wherein the phosphine ligand is an R form and the amine ligand is an optically active diamine with the chiral center carbon being an R,R form.

4. The ruthenium hydride complex as set forth in claim 1, wherein the phosphine ligand is an R form and the amine ligand is an optically active diamine with the chiral center carbon being an S,S form.

5. The ruthenium hydride complex as set forth in claim 1, wherein the phosphine ligand is an S form and the amine ligand is an optically active diamine with the chiral center carbon being an S,S form.

6. The ruthenium hydride complex as set forth in claim 1, wherein the phosphine ligand is an S form and the amine ligand is an optically active diamine with the chiral center carbon being an R,R form.

7. A method of preparing an alcohol compound wherein a ruthenium hydride complex expressed by the following general formula (1) is used to prepare an alcohol compound by reduction of a carbonyl compound under the non-presence of a strong base, under the presence of at least one compound selected from the group consisting of hydrogen and hydrogen donating compounds, and either in a reaction solvent or under solvent-free conditions, General formula (1):

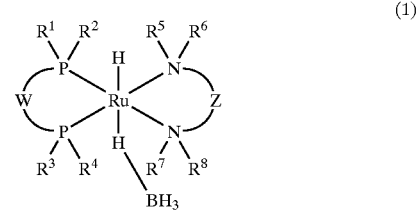

(1)

(wherein for R$^1$R$^2$P—W—PR$^3$R$^4$, W is a binaphthyl group, which is bonded to phosphorus atoms at positions 2 and 2' and may have one or more substituents at any of the other positions, each of R$^1$ to R$^4$ is the same or different hydrocarbon group that may or may not have one or more substituents, R$^1$ and R$^2$ may together form a carbon chain ring that may have one or more substituents, R$^3$ and R$^4$ may together form a carbon chain ring that may have one or more substituents, each of R$^5$ to R$^8$ is the same or different hydrocarbon group that may or may not have one or more substituents, Z is a hydrocarbon group that may or may not have one or more substituents, and each of the ligands of Ru may be positioned in any manner).

8. The method as set forth in claim 7 wherein an optically active alcohol compound is prepared by chiral reduction of an asymmetric carbonyl compound.

9. The method as set forth in claim 7 wherein said reaction solvent is a secondary alcohol.

10. The method as set forth in claim 7 wherein
said carbonyl compound is an asymmetric carbonyl compound that is sensitive to base.

11. The method as set forth in claim 10 wherein
said asymmetric carbonyl compound that is sensitive to base is an asymmetric carbonyl compound having at least one group selected from the group consisting of ester groups, epoxy groups, β-amino groups, and groups with an α, β-unsaturated bond.

12. A method of preparing an alcohol compound wherein
a ruthenium hydride complex expressed by the following general formula (1) is prepared and used without being isolated to prepare an alcohol compound by reduction of a carbonyl compound under the non-presence of a strong base and under the presence of at least one compound selected from the group consisting of hydrogen and hydrogen donating compounds, General formula (1):

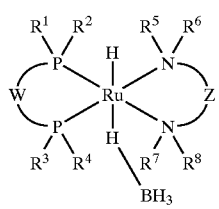

(1)

(wherein for R$^1$R$^2$P—W—PR$^3$R$^4$, W is a binaphthyl group, which is bonded to phosphorus atoms at positions 2 and 2' and may have one or more substituents at any of the other positions, each of R$^1$ to R$^4$ is the same or different hydrocarbon group that may or may not have one or more substituents, R$^1$ and R$^2$ may together form a carbon chain ring that may have one or more substituents, R$^3$ and R$^4$ may together form a carbon chain ring that may have one or more substituents, each of R$^5$ to R$^8$ is the same or different hydrocarbon group that may or may not have one or more substituents, Z is a hydrocarbon group that may or may not have one or more substituents, and each of the ligands of Ru may be positioned in any manner).

13. The method as set forth in claim 12 wherein
an optically active alcohol compound is prepared by chiral reduction of an asymmetric carbonyl compound.

14. The method as set forth in claim 12 wherein
said reaction solvent is a secondary alcohol.

15. The method as set forth in claim 12 wherein
said carbonyl compound is an asymmetric carbonyl compound that is sensitive to base.

16. The method as set forth in claim 15 wherein
said asymmetric carbonyl compound that is sensitive to base is an asymmetric carbonyl compound having at least one group selected from the group consisting of ester groups, epoxy groups, β-amino groups, and groups with an α, β-unsaturated bond.

17. A method of separating racemic carbonyl compounds wherein
a ruthenium hydride complex expressed by the following general formula (1) is used to selectively reduce one enantiomer among carbonyl compounds which are a mixture of different enantiomers to thereby obtain the other enantiomer, under the non-presence of a strong base, under the presence of at least one selected from the group consisting of hydrogen and hydrogen donating compounds, and either in a reaction solvent or under solvent-free conditions, General formula (1):

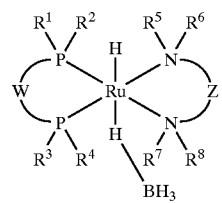

(1)

(wherein for R$^1$R$^2$P—W—PR$^3$R$^4$, W is a binaphthyl group, which is bonded to phosphorus atoms at positions 2 and 2' and may have one or more substituents at any of the other positions, each of R$^1$ to R$^4$ is the same or different hydrocarbon group that may or may not have one or more substituents, R$^1$ and R$^2$ may together form a carbon chain ring that may have one or more substituents, R$^3$ and R$^4$ may together form a carbon chain ring that may have one or more substituents, each of R$^5$ to R$^8$ is the same or different hydrocarbon group that may or may not have one or more substituents, Z is a hydrocarbon group that may or may not have one or more substituents, and each of the ligands of Ru may be positioned in any manner).

18. The method as set forth in claim 17, wherein
said carbonyl compounds are selected from the group consisting of α-alkyl ketones, α-alkoxy ketones, and α-amino ketones.

19. The method as set forth in claim 17 wherein
said reaction solvent is a secondary alcohol.

* * * * *